US009529025B2

(12) United States Patent
Moul et al.

(10) Patent No.: US 9,529,025 B2
(45) Date of Patent: Dec. 27, 2016

(54) SYSTEMS AND METHODS FOR MEASURING THE FREQUENCY OF SIGNALS GENERATED BY HIGH FREQUENCY MEDICAL DEVICES (71) Applicant: COVIDIEN LP, Mansfield, MA (US)

(72) Inventors: Wayne L. Moul, Loveland, CO (US); Robert J. Behnke, II, Erie, CO (US); Scott E. M. Frushour, Boulder, CO (US); Jeffrey L. Jensen, Boulder, CO (US)

(73) Assignee: COVIDIEN LP, Mansfield, MA (US)

( * ) Notice: Subject to any disclaimer, the term of this patent is extended or adjusted under 35 U.S.C. 154(b) by 891 days.

(21) Appl. No.: 13/898,632

(22) Filed: May 21, 2013

(65) Prior Publication Data

US 2014/0002056 A1 Jan. 2, 2014

Related U.S. Application Data (60) Provisional application No. 61/666,071, filed on Jun. 29, 2012.

(51) Int. Cl.
*G01R 23/02* (2006.01)
*G01R 23/00* (2006.01)
*G01R 25/00* (2006.01)

(52) U.S. Cl.
CPC ............... *G01R 23/00* (2013.01); *G01R 25/00* (2013.01)

(58) Field of Classification Search
CPC ..................... H01L 2224/48247; G01N 21/64; G01R 31/2637; G01R 27/28; G01R 31/2822

(Continued)

(56) References Cited

U.S. PATENT DOCUMENTS 5,966,053 A * 10/1999 Durig .................. B82Y 35/00
331/116 M
6,620,157 B1 9/2003 Dabney et al.
(Continued)

FOREIGN PATENT DOCUMENTS

DE 179607 C 3/1905
DE 390937 C 3/1924
(Continued)

OTHER PUBLICATIONS

Wald et al., "Accidental Burns", JAMA, Aug. 16, 1971, vol. 217, No. 7, pp. 916-921.
(Continued)

*Primary Examiner* — Melissa Koval
*Assistant Examiner* — Trung Nguyen (57) ABSTRACT Systems and corresponding methods for determining characteristics of an output signal generated by a high-frequency medical device using low-frequency measurement systems are disclosed. A digital measurement system includes an oscillator, a mixer, and a controller coupled to each other. The oscillator provides a reference signal having a second frequency. The mixer generates a down-converted signal based on the output signal and the reference signal. The controller then determines a characteristic of the output signal (e.g., frequency or phase) based on the down-converted signal. An analog measurement system includes a filter having a center frequency, a rectifier, and a controller. The filter filters the output signal and the rectifier rectifies the filtered signal. The controller samples the rectified signal and determines a characteristic of the output signal based on the level of the rectified signal. The reference signal controller may adjust a characteristic of the output signal based on the determined frequency and/or phase of the output signal.

16 Claims, 4 Drawing Sheets (58) Field of Classification Search
USPC ...... 324/76.11, 76.39–76.54, 76.68, 85, 520, 324/633, 667, 674, 681, 727, 600
See application file for complete search history.

(56) References Cited

U.S. PATENT DOCUMENTS

| | | |
|---|---|---|
| 6,652,514 B2 | 11/2003 | Ellman et al. |
| 6,994,707 B2 | 2/2006 | Ellman et al. |
| 7,058,372 B1 | 6/2006 | Pardoen et al. |
| 7,175,618 B2 | 2/2007 | Dabney et al. |
| 7,190,933 B2 | 3/2007 | De Ruijter et al. |
| 7,333,859 B2 | 2/2008 | Rinaldi et al. |
| D574,323 S | 8/2008 | Waaler |
| 7,479,140 B2 | 1/2009 | Ellman et al. |
| 7,525,398 B2 | 4/2009 | Nishimura et al. |
| 8,049,516 B2 | 11/2011 | Hancock et al. |
| 2002/0022836 A1 | 2/2002 | Goble et al. |
| 2005/0015125 A1* | 1/2005 | Mioduski ............ A61B 18/1233 607/102 |
| 2006/0155270 A1 | 7/2006 | Hancock et al. |
| 2006/0224053 A1 | 10/2006 | Black et al. |
| 2008/0234574 A1 | 9/2008 | Hancock et al. |
| 2010/0168730 A1 | 7/2010 | Hancock et al. |
| 2012/0087651 A1* | 4/2012 | Hwang ................ G01N 22/00 398/25 |
| 2013/0035679 A1 | 2/2013 | Orszulak |
| 2013/0053840 A1 | 2/2013 | Krapohl et al. |
| 2013/0066311 A1 | 3/2013 | Smith et al. |
| 2013/0067725 A1 | 3/2013 | Behnke, II et al. |
| 2013/0072920 A1 | 3/2013 | Behnke, II et al. |
| 2013/0072921 A1 | 3/2013 | Behnke, II et al. |
| 2013/0072922 A1 | 3/2013 | Behnke, II et al. |
| 2013/0072923 A1 | 3/2013 | Behnke, II et al. |
| 2013/0079673 A1 | 3/2013 | Stein et al. |
| 2013/0190751 A1 | 7/2013 | Brannan |
| 2013/0193952 A1 | 8/2013 | Krapohl |
| 2013/0197510 A1 | 8/2013 | Heckel |
| 2013/0197874 A1 | 8/2013 | Heckel |

FOREIGN PATENT DOCUMENTS

| | | |
|---|---|---|
| DE | 1099658 B | 2/1961 |
| DE | 1139927 B | 11/1962 |
| DE | 1149832 B | 6/1963 |
| DE | 1439302 A1 | 1/1969 |
| DE | 2439587 A1 | 2/1975 |
| DE | 2455174 A1 | 5/1975 |
| DE | 2407559 A1 | 8/1975 |
| DE | 2602517 A1 | 7/1976 |
| DE | 2504280 A1 | 8/1976 |
| DE | 2540968 A1 | 3/1977 |
| DE | 2820908 A1 | 11/1978 |
| DE | 2803275 A1 | 8/1979 |
| DE | 2823291 A1 | 11/1979 |
| DE | 2946728 A1 | 5/1981 |
| DE | 3143421 A1 | 5/1982 |
| DE | 3045996 A1 | 7/1982 |
| DE | 3120102 A1 | 12/1982 |
| DE | 3510586 A1 | 10/1986 |
| DE | 3604823 A1 | 8/1987 |
| DE | 3904558 A1 | 8/1990 |
| DE | 3942998 A1 | 7/1991 |
| DE | 4206433 A1 | 9/1993 |
| DE | 4339049 A1 | 5/1995 |
| DE | 19506363 A1 | 8/1996 |
| DE | 19717411 A1 | 11/1998 |
| DE | 19848540 A1 | 5/2000 |
| DE | 10 2008058737 A1 | 4/2010 |
| EP | 0 246 350 A1 | 11/1987 |
| EP | 267403 A2 | 5/1988 |
| EP | 296777 A2 | 12/1988 |
| EP | 0309942 A2 | 4/1989 |
| EP | 310431 A2 | 4/1989 |
| EP | 325456 A2 | 7/1989 |
| EP | 336742 A2 | 10/1989 |
| EP | 390937 A1 | 10/1990 |
| EP | 0503200 A2 | 9/1992 |
| EP | 0 556 705 A1 | 8/1993 |
| EP | 569130 A1 | 11/1993 |
| EP | 608609 A2 | 8/1994 |
| EP | 617925 A1 | 10/1994 |
| EP | 694291 A1 | 1/1996 |
| EP | 0 836 868 A2 | 4/1998 |
| EP | 870473 A2 | 10/1998 |
| EP | 0878169 A1 | 11/1998 |
| EP | 880220 A2 | 11/1998 |
| EP | 0 882 955 A1 | 12/1998 |
| EP | 0640317 B1 | 9/1999 |
| EP | 1051948 A2 | 11/2000 |
| EP | 1053720 | 11/2000 |
| EP | 1146827 A1 | 10/2001 |
| EP | 1151725 A1 | 11/2001 |
| EP | 1263181 A1 | 12/2002 |
| EP | 1278007 | 1/2003 |
| EP | 1293171 A2 | 3/2003 |
| EP | 1366724 A1 | 12/2003 |
| EP | 1472984 | 11/2004 |
| EP | 1495712 A1 | 1/2005 |
| EP | 1500378 A1 | 1/2005 |
| EP | 1535581 | 6/2005 |
| EP | 1594392 A2 | 11/2005 |
| EP | 1609430 | 12/2005 |
| EP | 1645235 A1 | 4/2006 |
| EP | 1681026 A2 | 7/2006 |
| EP | 1707143 | 10/2006 |
| EP | 1707144 A1 | 10/2006 |
| EP | 1744354 A2 | 1/2007 |
| EP | 1776929 A1 | 4/2007 |
| EP | 1810628 | 7/2007 |
| EP | 1810630 A1 | 7/2007 |
| EP | 1810631 A2 | 7/2007 |
| EP | 1810632 A1 | 7/2007 |
| EP | 1810633 A2 | 7/2007 |
| EP | 1810634 A1 | 7/2007 |
| EP | 1849425 A1 | 10/2007 |
| EP | 1854423 A2 | 11/2007 |
| EP | 1862137 A1 | 12/2007 |
| EP | 1994904 | 11/2008 |
| EP | 2025297 A2 | 2/2009 |
| EP | 2100566 A1 | 9/2009 |
| EP | 2111812 A2 | 10/2009 |
| EP | 2253286 A1 | 11/2010 |
| FR | 1 275 415 A | 11/1961 |
| FR | 1 347 865 A | 1/1964 |
| FR | 2 313 708 A1 | 12/1976 |
| FR | 2364461 A1 | 4/1978 |
| FR | 2 502 935 A1 | 10/1982 |
| FR | 2 517 953 A1 | 6/1983 |
| FR | 2 573 301 A1 | 5/1986 |
| GB | 607850 A | 9/1948 |
| GB | 702510 A | 1/1954 |
| GB | 855459 A | 11/1960 |
| GB | 902775 A | 8/1962 |
| GB | 1290304 A | 9/1972 |
| GB | 2154881 A | 9/1985 |
| GB | 2164473 A | 3/1986 |
| GB | 2214430 A | 9/1989 |
| GB | 2331247 A | 5/1999 |
| GB | 2358934 A | 8/2001 |
| GB | 2434872 A | 8/2007 |
| JP | 63 005876 A | 1/1988 |
| JP | 2002-065690 A | 3/2002 |
| SU | 166452 | 11/1964 |
| SU | 727201 A2 | 4/1980 |
| WO | 92/06642 | 4/1992 |
| WO | 92/07622 A1 | 5/1992 |
| WO | 93/20747 A1 | 10/1993 |
| WO | 93/24066 A1 | 12/1993 |
| WO | 94/10922 A1 | 5/1994 |
| WO | 94/24949 A1 | 11/1994 |
| WO | 94/28809 A1 | 12/1994 |
| WO | 95/09577 A1 | 4/1995 |
| WO | 95/18575 A1 | 7/1995 |
| WO | 95/19148 A1 | 7/1995 |

(56) References Cited

FOREIGN PATENT DOCUMENTS

| | | | |
|---|---|---|---|
| WO | 95/25471 | A2 | 9/1995 |
| WO | 95/25472 | A1 | 9/1995 |
| WO | 96/02180 | A2 | 2/1996 |
| WO | 96/04860 | A1 | 2/1996 |
| WO | 96/08794 | A1 | 3/1996 |
| WO | 96/18349 | A2 | 6/1996 |
| WO | 96/29946 | A1 | 10/1996 |
| WO | 96/39085 | A1 | 12/1996 |
| WO | 96/39086 | A1 | 12/1996 |
| WO | 96/39088 | A1 | 12/1996 |
| WO | 96/39914 | A1 | 12/1996 |
| WO | 97/06739 | A2 | 2/1997 |
| WO | 97/06740 | A2 | 2/1997 |
| WO | 97/06855 | A2 | 2/1997 |
| WO | 97/10763 | A1 | 3/1997 |
| WO | 97/11648 | A2 | 4/1997 |
| WO | 97/17029 | A1 | 5/1997 |
| WO | 97/43971 | A2 | 11/1997 |
| WO | 98/07378 | A1 | 2/1998 |
| WO | 98/18395 | A1 | 5/1998 |
| WO | 98/27880 | | 7/1998 |
| WO | 99/12607 | A1 | 3/1999 |
| WO | 99/56647 | A1 | 11/1999 |
| WO | 00/48672 | A1 | 8/2000 |
| WO | 00/54683 | A1 | 9/2000 |
| WO | 01/01847 | | 1/2001 |
| WO | 02/00129 | | 1/2002 |
| WO | 02/11634 | | 2/2002 |
| WO | 02/32333 | | 4/2002 |
| WO | 02/32335 | | 4/2002 |
| WO | 02/45589 | | 6/2002 |
| WO | 02/47565 | | 6/2002 |
| WO | 02/053048 | A1 | 7/2002 |
| WO | 02/088128 | A1 | 11/2002 |
| WO | 03/047446 | A1 | 6/2003 |
| WO | 03/090635 | A1 | 11/2003 |
| WO | 03/092520 | A1 | 11/2003 |
| WO | 03/090630 | A3 | 4/2004 |
| WO | 2004/028385 | A1 | 4/2004 |
| WO | 2004/043240 | A2 | 5/2004 |
| WO | 2004/047659 | A2 | 6/2004 |
| WO | 2004/052182 | A2 | 6/2004 |
| WO | 2004/073488 | | 9/2004 |
| WO | 2004/098385 | A2 | 11/2004 |
| WO | 2004/103156 | | 12/2004 |
| WO | 2005/046496 | A1 | 5/2005 |
| WO | 2005/048809 | | 6/2005 |
| WO | 2005/050151 | | 6/2005 |
| WO | 2005/060365 | A2 | 7/2005 |
| WO | 2005/060849 | A1 | 7/2005 |
| WO | 2005/115235 | A1 | 12/2005 |
| WO | 2005/117735 | A1 | 12/2005 |
| WO | 2006/050888 | A1 | 5/2006 |
| WO | 2006/105121 | A2 | 10/2006 |
| WO | 2007/055491 | A1 | 5/2007 |
| WO | 2007/067522 | A2 | 6/2007 |
| WO | 2007/076924 | A2 | 7/2007 |
| WO | 2007/105963 | A1 | 9/2007 |
| WO | 2008/002517 | A1 | 1/2008 |
| WO | 2008/003058 | A2 | 1/2008 |
| WO | 2008/011575 | A1 | 1/2008 |
| WO | 2008/043999 | A2 | 4/2008 |
| WO | 2008/044000 | A1 | 4/2008 |
| WO | 2008/044013 | A2 | 4/2008 |
| WO | 2008/053532 | A1 | 5/2008 |
| WO | 2008/070562 | A1 | 6/2008 |
| WO | 2008/071914 | A2 | 6/2008 |
| WO | 2008/101356 | A1 | 8/2008 |
| WO | 2008/110756 | A2 | 9/2008 |

OTHER PUBLICATIONS

Vallfors et al., "Automatically Controlled Bipolar Electrosoagulation-'COA-COMP'", Neurosurgical Review 7:2-3 (1984) pp. 187-190.

Sugita et al., "Bipolar Coagulator with Automatic Thermocontrol", J. Neurosurg., vol. 41, Dec. 1944, pp. 777-779.

Prutchi et al. "Design and Development of Medical Electronic Instrumentation", John Wiley & Sons, Inc. 2005.

Momozaki et al. "Electrical Breakdown Experiments with Application to Alkali Metal Thermal-to-Electric Converters", Energy conversion and Management; Elsevier Science Publishers, Oxford, GB; vol. 44, No. 6, Apr. 1, 2003 pp. 819-843.

Muller et al. "Extended Left Hemicolectomy Using the LigaSure Vessel Sealing System" Innovations That Work; Company Newsletter; Sep. 1999.

Ogden Goertzel Alternative to the Fourier Transform: Jun. 1993 pp. 485-487, Electronics World; Reed Business Publishing, Sutton, Surrey, BG vol. 99, No. 9. 1687.

Hadley I C D et al., "Inexpensive Digital Thermometer for Measurements on Semiconductors", International Journal of Electronics; Taylor and Francis. Ltd.; London, GB; vol. 70, No. 6 Jun. 1, 1991; pp. 1155-1162.

Burdette et al. "In Vivo Probe Measurement Technique for Determining Dielectric Properties at VHF Through Microwave Frequencies", IEEE Transactions on Microwave Theory and Techniques, vol. MTT-28, No. 4, Apr. 1980 pp. 414-427.

Richard Wolf Medical Instruments Corp. Brochure, "Kleppinger Bipolar Forceps & Bipolar Generator", 3 pp. Jan. 1989.

Astrahan, "A Localized Current Field Hyperthermia System for Use with 192-Iridium Interstitial Implants" Medical Physics, 9 (3), May/Jun. 1982.

Alexander et al., "Magnetic Resonance Image-Directed Stereotactic Neurosurgery: Use of Image Fusion with Computerized Tomography to Enhance Spatial Accuracy", Journal Neurosurgery, 83; (1995) pp. 271-276.

Geddes et al., "The Measurement of Physiologic Events by Electrical Impedence", Am. J. MI, Jan. Mar. 1964, pp. 16-27.

Cosman et al., "Methods of Making Nervous System Lesions", In William RH, Rengachary SS (eds): Neurosurgery, New York: McGraw-Hill, vol. 111, (1984), pp. 2490-2499.

Anderson et al., "A Numerical Study of Rapid Heating for High Temperature Radio Frequency Hyperthermia" International Journal of Bio-Medical Computing, 35 (1994) pp. 297-307.

Benaron et al., "Optical Time-of-Flight and Absorbance Imaging of Biologic Media", Science, American Association for the Advancement of Science, Washington, DC, vol. 259, Mar. 5, 1993, pp. 1463-1466.

Cosman et al., "Radiofrequency Lesion Generation and Its Effect on Tissue Impedance", Applied Neurophysiology 51: (1988) pp. 230-242.

Zlatanovic M., "Sensors in Diffusion Plasma Processing" Microelectronics 1995; Proceedings 1995; 20th International Conference CE on Nis, Serbia Sep. 12-14, 1995; New York, NY vol. 2 pp. 565-570.

Ni W. et al. "A Signal Processing Method for the Coriolis Mass Flowmeter Based on a Normalized . . . ", Journal of Applied Sciences-Yingyong Kexue Xuebao, Shangha CN, vol. 23 No. 2;(Mar. 2005); pp. 160-164.

Chicharo et al. "A Sliding Goertzel Algorith" Aug. 1996, pp. 283-297 Signal Processing, Elsevier Science Publishers B.V. Amsterdam, NL vol. 52 No. 3.

Bergdahl et al., "Studies on Coagulation and the Development of an Automatic Computerized Bipolar Coagulator" Journal of Neurosurgery 75:1, (Jul. 1991) pp. 148-151.

Cosman et al., "Theoretical Aspects of Radiofrequency Lesions in the Dorsal Root Entry Zone", Neurosurgery 15: (1984) pp. 945-950.

Goldberg et al., "Tissue Ablation with Radiofrequency: Effect of Probe Size, Gauge, Duration, and Temperature on Lesion Volume" Acad Radio (1995) vol. 2, No. 5, pp. 399-404.

Medtrex Brochure—Total Control at Full Speed, "The O.R. Pro 300", 1 p. Sep. 1998.

(56) References Cited

OTHER PUBLICATIONS

Valleylab Brochure "Valleylab Electroshield Monitoring System" 2 pp. Nov. 1995.
U.S. Appl. No. 10/406,690, Michael S. Klicek.
U.S. Appl. No. 10/573,713, Robert H. Wham.
U.S. Appl. No. 10/761,524, Robert Wham.
U.S. Appl. No. 11/242,458, Daniel J. Becker.
U.S. Appl. No. 13/426,204, Robert B. Smith.
U.S. Appl. No. 13/427,111, Daniel A. Joseph.
U.S. Appl. No. 13/442,460, James E. Krapohl.
U.S. Appl. No. 13/446,096, James H. Orszulak.
U.S. Appl. No. 13/469,960, Robert J. Behnke, II.
U.S. Appl. No. 13/485,083, Robert J. Behnke, II.
U.S. Appl. No. 13/587,400, James H. Orszulak.
U.S. Appl. No. 13/360,289, Heckel.
U.S. Appl. No. 13/360,306, Heckel.
U.S. Appl. No. 13/652,932, Wham.

* cited by examiner

SYSTEMS AND METHODS FOR MEASURING THE FREQUENCY OF SIGNALS GENERATED BY HIGH FREQUENCY MEDICAL DEVICES

CROSS REFERENCE TO RELATED APPLICATION

The present application claims the benefit of and priority to U.S. Provisional Application Ser. No. 61/666,017, filed on Jun. 29, 2012, the entire contents of which are incorporated herein by reference.

BACKGROUND

1. Technical Field

The present disclosure relates to systems and methods for measuring the output frequency of a high frequency medical device. More particularly, the present disclosure relates to systems and methods for measuring the output frequency of a high frequency generator using low frequency measurement techniques. Further, the present disclosure relates to systems and methods for maintaining the output frequency of a high frequency generator within an acceptable range.

2. Description of Related Art

During medical treatment procedures in which an electrosurgical generator is used to supply electrosurgical energy to an instrument for treatment of tissue, it is often useful to measure and/or monitor the output frequency of the generator. For generators operating at relatively low frequencies, e.g., frequencies below 1 MHz, it is relatively easy to measure the output frequency, for example, by known methods using the clock frequency of a measurement system.

However, for generators operating at relatively high frequencies, such as, for example, microwave generators operating above 300 MHz, and more typically above 900 MHz, it is much more difficult to measure the output frequency in a reliable and cost effective manner. This is so because at those high frequencies it is no longer possible to use the clock frequency of the measurement system.

The ability to measure the output frequency for high frequency medical devices is extremely useful for a number of reasons that allow for more efficient utilization of the equipment during a given procedure. One reason is that it is useful, if not necessary, during a procedure to keep the output frequency within a specific frequency band to ensure that the generator and/or medical device is operating within specific internationally recognized Industrial, Scientific and Medical (ISM) radio bands. In certain ISM bands, particularly those that relate to medical applications, there is only a limited set deviation allowed from the center frequency. Other reasons would be to meet a need to shift the output frequency for impedance matching purposes, or to adjust the phase of the generator's output.

In the example of the electrical performance of a microwave energy delivery system (e.g., a system including a generator, an energy delivery device, a waveguide configured to deliver a microwave energy signal from the generator to the energy delivery device, and an antenna) changes throughout the course of a treatment, for example, an ablation treatment in which tissue, such as tumor tissue, is targeted for destruction. The change in performance may be due to a change in the energy delivery device, a change in the tissue properties or a change in the delivery path. The ability to observe parameters, e.g., by measuring the output frequency of the generator during the procedure, indicative of these changes provides better control of the delivery of the microwave energy.

Accordingly, a need exists for reliable systems and methods for measuring the output frequency of a high frequency medical device using a low frequency measurement system and for maintaining the output frequency within an acceptable range.

SUMMARY

As used herein, the term "distal" refers to the portion that is being described which is further from a user, while the term "proximal" refers to the portion that is being described which is closer to a user.

The present disclosure describes systems and methods for measuring the output frequency of a medical device and/or generator operating at a frequency higher than a clock frequency of the measurement system.

Accordingly, a need exists for reliable systems and methods for measuring a high frequency output of a medical device using a low frequency measurement system and for maintaining the output frequency within an acceptable range.

According to an aspect of the present disclosure, a system for measuring a characteristic of an output signal generated by a generator, the output signal having a first frequency. The system includes an oscillator configured to provide a reference signal having a second frequency. The system also includes a mixer configured to generate a down-converted signal based on the output signal and the reference signal. Furthermore, the system includes a controller configured to operate at a clock frequency lower than the first frequency and to determine a characteristic of the output signal based on the down-converted signal.

According to another aspect of the present disclosure, the characteristic of the output signal may be frequency or phase.

According to a further aspect of the present disclosure, the output signal may be a digital signal or an analog signal.

According to another aspect of the present disclosure, the controller may be further configured to control the output signal based on the determined characteristic of the output signal.

According to a further aspect of the present disclosure, the reference signal may be a signal having a fixed or variable frequency.

According to another aspect of the present disclosure, the second frequency may be set to a frequency such that the difference between the first and reference signal frequencies is less than the clock frequency of the generator.

According to a further aspect of the present disclosure, the second frequency may be set equal to the first frequency.

According to another aspect of the present disclosure, the second frequency may be set to a frequency offset from the first frequency.

According to a further aspect of the present disclosure, the output signal may be a DC value when the output signal and the reference signal are locked to the same frequency.

According to another aspect of the present disclosure, the characteristic of the output signal may be frequency, and the system may further include an amplifier configured to amplify the output signal. The system may also include a second mixer configured to generate a second, down-converted signal based on the amplified output signal and the reference signal. The controller may be further configured to determine a phase of the amplified output signal based on the second, down-converted signal.

According to a further aspect of the present disclosure, the system may further include one or more sensors coupled to the output of the amplifier. The one or more sensors may be configured to sense the amplified output signal and provide the sensed, amplified output signal to the second mixer.

According to another aspect of the present disclosure, a system for measuring a high frequency output signal generated by a generator. The system includes a filter having a center frequency, the filter configured to filter the output signal to obtain a filtered signal. The system also includes a rectifier configured to rectify the filtered signal to obtain a rectified signal, and a microprocessor configured to sample the rectified signal and to determine a frequency of the output signal based on the level of the rectified signal.

According to another aspect of the present disclosure, the filter may be a notch filter or a band-pass filter.

According to a further aspect of the present disclosure, the filter may be configured to attenuate the output signal as the frequency of the output signal moves away from the center frequency.

According to another aspect of the present disclosure, the system may further include an amplifier configured to amplify the output signal, and a second filter having a second center frequency, the second filter configured to filter the amplified signal to obtain a second filtered signal. The system may further include a second rectifier configured to rectify the second filtered signal to obtain a second rectified signal. The microprocessor may be further configured to sample the second rectified signal and to determine a phase of the amplified output signal based on a level of the second rectified signal.

According to another aspect of the present disclosure, a method for measuring a characteristic of a high frequency output signal generated by a generator, the output signal having a first frequency that is higher than a clock frequency of a processor within the generator. The method includes the steps of generating a reference signal having a second frequency, and mixing the output signal and the reference signal to generate a down-converted signal reference signal. The method further includes the step of determining the characteristic of the output signal based on the down-converted signal.

Alternatively, the e characteristic may be frequency or phase reference signal.

Alternatively or in addition, the method may further include the step of verifying whether the characteristic of the output signal is within a predetermined range.

Alternatively or in addition, the method may further include the step of adjusting the frequency of the output signal to achieve a desired output impedance of the generator.

Alternatively or in addition, the method may further include the steps of amplifying the output signal, and mixing the amplified output signal and the reference signal to obtain a second down-converted signal. The method may also include determining the phase of the amplified output signal based on the second down-converted signal.

According to a further aspect of the present disclosure, a generator includes a first oscillator configured to generate an output signal having a first frequency that is higher than a clock frequency of the generator. The generator further includes a second oscillator configured to generate a reference signal having a second frequency. Also, the generator includes a mixer coupled to the first and second oscillators. The mixer is configured to generate a down-converted signal based on the output signal and the reference signal. Furthermore, the generator includes a controller configured to determine the first frequency based on the down-converted signal.

BRIEF DESCRIPTION OF THE DRAWINGS

Various aspects of the present disclosure are described hereinbelow with reference to the drawings, wherein.

DETAILED DESCRIPTION

Detailed embodiments of the present disclosure are described herein; however, it is to be understood that the disclosed embodiments are merely exemplary and may be embodied in various forms. Therefore, specific structural and functional details disclosed herein are not to be interpreted as limiting, but merely as a basis for the claims and as a representative basis for teaching one skilled in the art to employ the present disclosure in virtually any appropriately detailed structure.

For purposes of describing the presently disclosed system and methods for measuring and/or adjusting the output frequency of a high frequency generator using a low frequency measurement system the detailed description that follows will use the illustrative embodiment of a system for delivering microwave energy for microwave therapy or treatment to a patient. However, it should be understood that such a high frequency system is for illustrative purposes and in no way limiting on the scope of the present disclosure.

Figure 1:
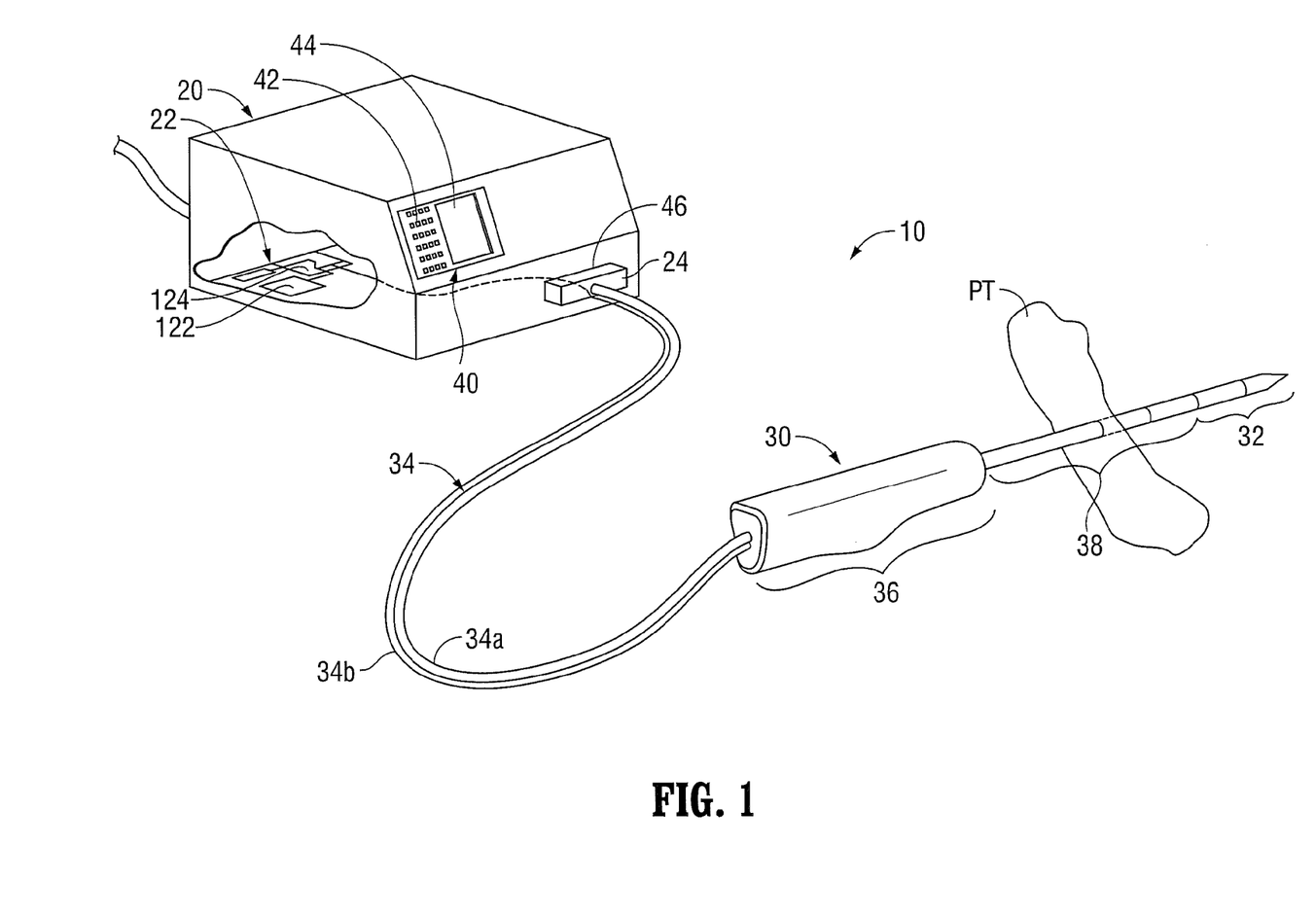
FIG. 1 is a perspective view of a microwave energy delivery system according to an embodiment of the present disclosure.

Referring now to FIG. 1, a system for delivering microwave energy for microwave therapy, according to an embodiment of the present disclosure, is generally designated by reference numeral 10. The microwave energy delivery system 10 includes an electrosurgical generator 20 with a control circuit 22 for controlling the operation of the electrosurgical generator 20 and a microwave energy delivery device 30 electrically coupled to the electrosurgical generator 20 via a transmission line 34. Microwave energy delivery device 30 includes an antenna 32 disposed at the distal end of a shaft 38, which extends from a handpiece 36.

Transmission line 34 includes a coaxial cable 34*a* (i.e., a waveguide) and an auxiliary cable 34*b*. The coaxial cable 34*a* is configured to deliver a microwave energy signal between the electrosurgical generator 20 and the handpiece 36 of the microwave energy delivery device 30. The auxiliary cable 34*b* is configured to deliver one or more signals between the handpiece 36 and the electrosurgical generator 20. The one or more signals delivered between the handpiece 36 and the electrosurgical generator 20 may include a DC power signal for powering circuitry in the handpiece 36 and an information signal containing real-time or historical information related to a condition and/or a quality of the microwave energy signal at the handpiece 36, the shaft 38, and/or the antenna 32 that radiates therapeutic energy therefrom.

A transmission line connector 24 disposed on the proximal end of the transmission line 34 connects to a transmission line receiver 46 on the electrosurgical generator 20. A distal end of the transmission line 34 connects to the microwave energy delivery device 30.

Electrosurgical generator 20 may include an operator interface 40 having a keypad 42 for entering parameters related to electrosurgical generator 20, the microwave energy delivery device 10 and/or parameters related to the delivery of microwave energy. Display 44 may indicate or graph one or more parameters related to the delivery of microwave energy and/or one or more parameters related to the microwave generator 20, transmission line 34 and/or microwave energy delivery device 10.

One suitable microwave energy delivery device 30 for use in connection with the present disclosure is a tissue penetrating microwave energy delivery device sold by Covidien under the trademark Evident™ Microwave Ablation Surgical Antennas, although the embodiments described herein may be suitable for any device capable of delivering microwave energy or the like. The embodiments described herein may also be applied to any suitable energy delivery device as explained in more detail below.

Figure 2:
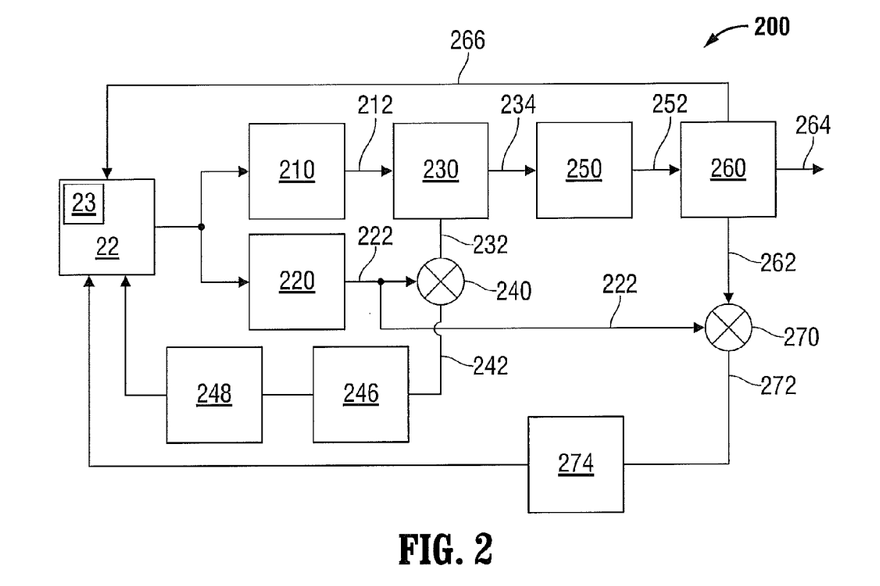
FIG. 2 is a schematic block diagram of a system using a digital approach for determining the output frequency of a medical device in accordance with an illustrative embodiment of the present disclosure.

FIG. 2 shows a schematic block diagram of a digital system 200 for determining the output frequency of a typical electrosurgical generator 20. The system 200 may be part of the generator 20, a stand alone box (not shown) connected between the microwave energy delivery device 30 and the generator 20, and/or within the microwave energy delivery device 30.

The digital system 200 includes a controller 22, which may be a microprocessor, a central processing unit, or other similar device. The controller 22 is configured to control the generation and delivery of a microwave energy signal at a predetermined frequency by controlling a first oscillator 210.

The first oscillator 210 generates and provides a first high frequency microwave signal 212 to the coupler 230. The first oscillator 210 may generate a signal having a fixed frequency, a signal having a variable frequency, or a signal having two or more related or unrelated frequencies at which the microwave energy delivery device 30 (See FIG. 1) is configured to resonate.

The second oscillator 220 generates and provides a reference signal 222 to the first mixer 240 and the second mixer 270. The reference signal 222 is a reference signal that may be a fixed frequency or a variable frequency controlled by the controller 22. The first mixer 240 multiplies the output signal 212 by the reference signal 222 to generate a down-converted signal 242. The down-converted signal 242 includes a first signal having a frequency equal to the difference between the frequencies of the output signal 212 and the reference signal 222, and a second signal having a frequency equal to the sum of the frequencies of the output signal 212 and the reference signal 222. The frequency of the reference signal 222 is selected such that the difference between the frequency of the output signal 212 and the frequency of the reference signal 222 is less than the clock frequency of the processor 122 within the generator 20.

The reference signal 222 may have a lower frequency than the frequency of the output signal 212. For example, if the frequency of the main signal is about 915 MHz and the frequency of the reference signal 222 is about 914 MHz, then the first down-converted signal 242 from the first mixer 240 is 1 MHz.

The first down-converted signal 242 is then passed through a filter 246 and an analog-to-digital converter (ADC) 248. The filter 246 may be a lowpass filter that passes the baseband signal, i.e., the first signal of the first down-converted signal 242, while rejecting the second signal of the first down-converted signal 242. The low-pass filter may be a finite impulse response (FIR) filter, an infinite impulse response (IIR) filter, or a cascaded integrator-comb filter.

Then, the frequency detector 23, such as a Fast Fourier Transform algorithm, is used to determine the frequency of the filtered first down-converted signal 242. The controller 22 then uses the frequency of the reference signal 222 and the detected frequency of the first down-converted signal 242 to determine the frequency of the output signal 212. Based on the determined frequency of the output signal 212, the controller 22 can then determine whether the frequency of the output signal 212 is within a predefined range. One advantage of measuring the frequency of the signal output from the first oscillator 210 is that its power level is constant.

Alternatively, the second oscillator 220 may be configured to generate a reference signal 222 having a frequency approximately equal to the frequency of the output signal 212. The first mixer 240 then generates a first down-converted signal 242 based on the output signal 212 and the reference signal 222. The first down-converted signal 242 is then provided to the controller 22 via the filter 246 and the ADC 248. As described above, the filtered first down-converted signal 242 has a frequency equal to the difference in frequency between the output signal 212 and the reference signal 222.

When the frequency of the reference signal 222 is set equal to the frequency of the output signal 212, or, in other words, when the frequency of the reference signal 222 is locked onto the frequency of the output signal 212, the first down-converted signal 242 generated by the first mixer 240 is a DC value.

The first down-converted signal 242 is sent to controller 22. After the first down-converted signal 242 is sampled by the frequency detector 23, the controller 22 determines whether the output signal 212 and reference signal are approximately equal, i.e., whether the frequency of the output signal is accurate. If the first down-converted signal 242 is greater than or less than zero, then the frequency of the output signal 212 is not accurate. The controller 22 may then correct the frequency of the output signal 212, and/or other similar parameters to correct the frequency of the output signal 212.

In embodiments, an alarm or LED light (not shown) may indicate to the user that the frequency of the output signal 212 is not correct, which may indicate that the user should stop using the device 30, adjust the frequency, and/or modify other parameters on the generator 20. In embodiments, the frequency difference between the output signal 121 and the reference signal 222 may need to be greater than a predetermined threshold before a controller 22 modifies one or more parameters and/or a user is notified and/or modifies one or more parameters of the generator 20.

In some embodiments, the frequency of the reference signal 222 may be offset from the frequency of the output signal 212. For example, the frequency offset may be about 0.1-2 MHz. Alternatively, the frequency offset may be determined by an isolation required between frequency bands and the type or caliber of filter used. Also the offset may be specified in terms of octaves, decades, mathematical model, and/or an isolatable variable. In other embodiments, the reference signal 222 may be at a higher frequency than the output signal 212.

The reference signal 222 may have a variable frequency. For example, the frequency of the reference signal 222 may adjust relative to variations in the frequency of the output signal 212. The output signal 212 may be set to a frequency range in a user- or controller-specified program. Alternatively, the reference signal 212 may have a fixed frequency. For example, the fixed frequency of the reference signal 212 may range from about 10 MHz to about 10 GHz.

The second output 234 of the coupler 230 provides the output signal 212 to an amplifier 250. The amplifier 250 receives and amplifies the high frequency microwave output signal 212 to a desirable energy level. Amplifier 250 may include a single-stage or multi-stage amplifier and may include one or more signal conditioning circuits or filters (not shown) such as, for example, a low-pass filter circuit, a high-pass filter circuit or a bandpass filter circuit. The gain of Amplifier 250 may be fixed or controlled by a suitable controller, such as, for example, a control algorithm in a supervisory control system (not shown). Alternatively, the gain of the amplifier 250 may be manually adjusted by a clinician through the keypad 42 (See FIG. 1).

The amplified signal 252 is supplied to one or more sensors 260 strategically located for sensing various properties or conditions, e.g., tissue impedance, voltage at the tissue site, current at the tissue site, etc. The sensors are provided with leads or may be wireless for transmitting information to the controller 22. The one or more sensors 260 may include control circuitry that receives information from multiple sensors, and provides the information and the source of the information (e.g., the particular sensor providing the information) to the controller 22.

More particularly, the one or more sensors 260 may include a real-time voltage sensing system and a real-time current sensing system for sensing real-time values related to applied voltage and current at the surgical site. Additionally, an RMS voltage sensing system and an RMS current sensing system may be included for sensing and deriving RMS values for applied voltage and current at the surgical site.

The controller 22 includes a microprocessor 122 having a memory 124 which may be volatile type memory (e.g., RAM) and/or non-volatile type memory (e.g., flash media, disk media, etc.). The microprocessor 122 includes an output port connected to the generator 20 that allows the microprocessor 122 to control the output of the generator 20 according to either open and/or closed loop control schemes.

A closed loop control scheme generally includes a feedback control loop 266 wherein the one or more sensors 260 provides feedback 266 to the controller 22 (i.e., information obtained from one or more sensing mechanisms for sensing various parameters such as tissue impedance, tissue temperature, forward and reflected current and/or voltage, etc.). The controller 22 then signals the generator 20 which then adjusts the output electromagnetic energy. The controller 22 also receives input signals from the input controls of the generator 22 and/or instrument 30. The controller 22 utilizes the input signals to adjust the power output of the generator 20 and/or instructs the generator 20 to perform other control functions.

The microprocessor 122 is capable of executing software instructions for processing data received by the one or more sensors 260, and for outputting control signals to the generator 20, accordingly. The software instructions, which are executable by the controller 22, are stored in the memory 124 of the controller 22.

The amplified signal 252 is supplied to the microwave energy delivery device 30 via output 264. Further, the amplified signal 252 is supplied via the one or more sensors 260 and/or directly to the second mixer 270. If the amplified signal 252 is supplied through the one or more sensors 260, then a sensed signal 262 is supplied to the second mixer 270.

The second mixer 270 generates a second down-converted signal 272 based on the amplified signal 252 (or sensed signal 262) and the reference signal 222. In embodiments, the second mixer 270 multiplies the amplified signal 252 by the reference signal 222 to obtain the second down-converted signal 272. The second down-converted signal 272 is sent to the controller 22 via filter 274. Alternatively, a phase locked-loop circuit or voltage controlled oscillator may be used instead of a mixer to determine the phase difference. If the phases are the same, then a phase signal, which is about zero, is sent to controller 22 and indicates that the phase has not shifted. If the second down-converted signal 272 is greater than or less than zero, then the phase of the amplified signal 252 has shifted. The controller 22 may then correct the frequency of the output signal 212, adjust the gain of amplifier 250, turn the generator 20 off, and/or other similar functions to correct the frequency of the output signal 212. Alternatively, an alarm or LED light (not shown) may indicate to the user that the phase has shifted, which may indicate that the user should stop using the instrument 30, adjust the frequency, and/or modify other parameters of the generator 20. In an alternative embodiment, the phase shift may need to be greater than a predetermined threshold before the controller 22 modifies one or more parameters, turns the generator 20 off, and/or a user is notified and/or modifies one or more parameters.

The controller 22 is configured to receive measurement signals related to the first down-converted signal 242, the second down-converted signal 272, and/or the feedback signal 266. For example, the controller 22 receives the first down-converted signal 242 from the first mixer 240 and receives a second down-converted signal 272 from the second mixer 270. The controller 22, by receiving information related to the frequency, phase, and/or sensor information is able to determine the frequency and phase shift of the output 264 of the generator 20 and/or if the generator 20 is functioning within a specified frequency range. Additionally, the controller 22 can adjust the frequency of the output signal 212 to vary the impedance of the generator 20 using the impedance measured by the sensor 260 and the measured frequency of the output signal 212.

Figure 3:
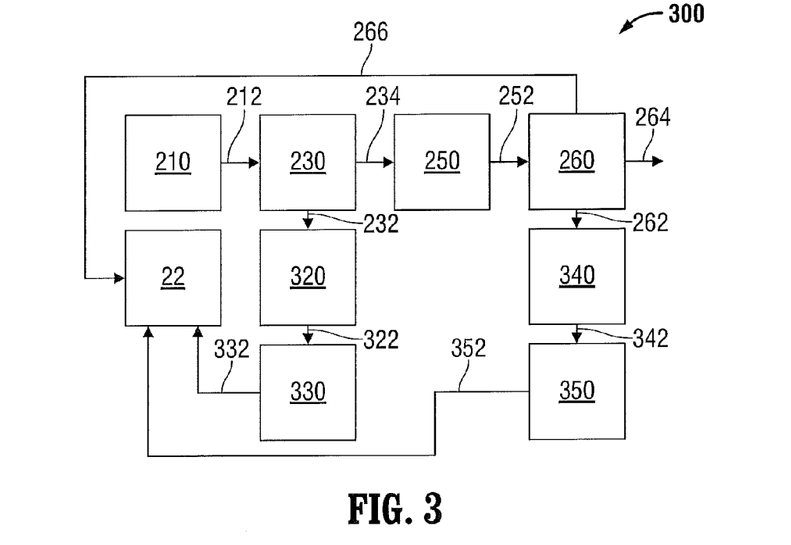
FIG. 3 is a schematic block diagram of a system using an analog approach for determining the output frequency of a medical device in accordance with an another illustrative embodiment of the present disclosure.

Referring to FIG. 3, an analog system 300 for determining the output frequency of an electrosurgical generator will now be described. The system 300 may be part of the generator 20, a stand alone box (not shown) connected between the microwave energy delivery device 30 and the generator 20, and/or within the microwave energy delivery device 30.

The analog system 300 includes a controller 22 and a first oscillator 210 similar to those used in the digital system 200 described above. The output signal 212 is supplied to coupler 230. The first output 232 of the coupler 230 provides the output signal 212 to a first filter 320.

The first filter 320 may be a notch filter, band-pass filter, or other suitable filter. The first filter 320 is configured with a center frequency set to a desired frequency of the output signal 212, e.g., the frequency set by the user through inputs 42 (See FIG. 1).

The first filter 320 provides a filtered signal 322 to a first rectifier 330. The rectifier 330 may include any type of suitable diode such as Zener diode, Schottky diode, tunnel diode and the like. The rectifier 330 sends a rectified signal 332 to the controller 22.

When the frequency of the output signal 212 moves above or below the center frequency, the first filter 320 attenuates the output signal 232 by an amount which depends upon how far the frequency of the output signal 232 is from the center frequency. The first filter provides a first filtered signal 322 to the first rectifier 330. The first rectifier 320 rectifies the first filtered signal 322 and outputs the first rectified signal 332 to the controller 22. The first rectified signal 332 may be a DC signal. The controller 22 and/or the microprocessor 122 sample the first rectified signal 332 and determine the frequency shift. If the frequency shift is nonzero, outside a predefined range, or greater than a predetermined threshold, then the controller 22 informs the user through an alarm or LED as previously noted, adjusts the frequency generated by the first oscillator 210, adjusts one or more parameters of the generator 20, and/or shuts the generator 20 off. Alternatively, in response to the notification from the controller 22, the user may adjust one or more parameters of the generator 20, stop using the instrument 30, and/or turn off the generator 20.

The second output 234 of coupler 230 provides the output signal 212 to an amplifier 250. The output signal 212 is amplified and the amplified signal is provided to sensors 260, the instrument 30 via output 264, and/or to a second filter 340. The second filter 340 may be a notch filter, band-pass filter, or other suitable filter. The second filter 340 is configured with a center frequency set to a desired phase of the output signal 212, e.g., zero phase.

The second filter 340 provides a second filtered signal 342 to a second rectifier 350. As with the rectifier 330, the rectifier 350 may include any type of suitable diode such as Zener diode, Schottky diode, tunnel diode and the like. The rectifier 350 sends a second rectified signal 352 to the controller 22. The second rectified signal 352 may be a DC signal.

When the phase of the output signal 212 shifts above or below the desired phase, the second filter 340 attenuates the signal and outputs a second filtered signal 342 to the second rectifier 350. The second rectifier 350 rectifies the second filtered signal 342 and outputs the second rectified signal 352 to the controller 22. The controller 22 and/or the microprocessor 122 samples the second rectified signal 352 and determines the phase shift. If the phase shift is greater than zero or greater than a predetermined threshold, then the controller informs the user through an alarm or LED, adjusts the frequency supplied through the first oscillator 210, adjust the gain of amplifier 250, adjusts one or more parameters of the generator 20, and/or shuts the generator 20 off. Alternatively, in response to the notification from the controller 22, the user may adjust one or more parameters of the generator 20, stop using the instrument 30, and/or turn off the generator 20.

Figure 4:
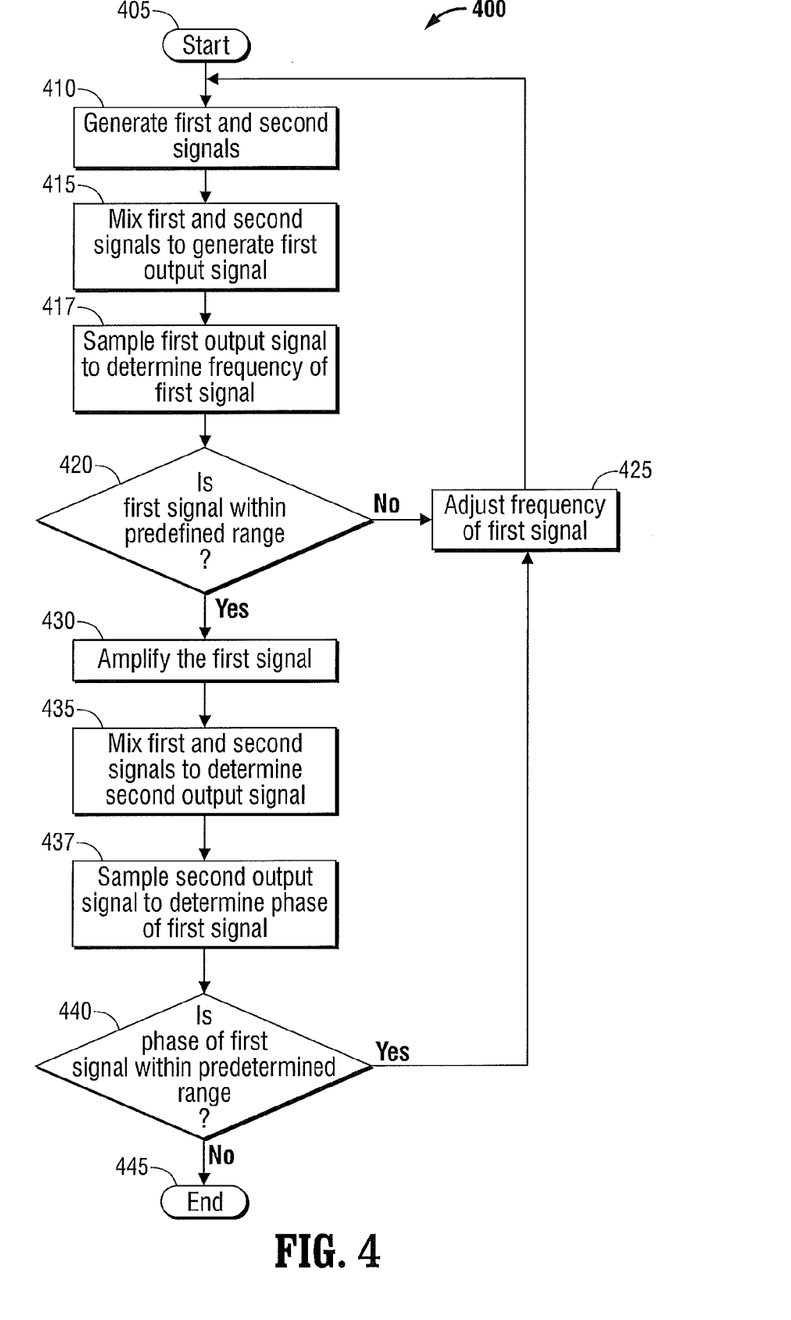
FIG. 4 is a flow diagram of a method for maintaining an output frequency of a medical device using the digital approach of FIG. 2 in accordance with one illustrative embodiment of the present disclosure.

Referring now to FIG. 4 in conjunction with FIG. 2, a digital approach process 400 for maintaining an output frequency of a generator 20 will now be described. The process 400 starts at step 405 and at step 410, in which a output signal 212 and a reference signal 222 are generated by first and second oscillators 210, 220. The output signal 212 and/or the reference signal 222 may be provides by oscillators 210, 220 and the oscillators 210, 220 may or may not be controlled by a controller 22. The desired frequency of the output signal 212 may programmed by a user through a user interface 42 and/or from a program within the controller 22. The reference signal 222 may be provided at the same frequency as the output signal 212, at a frequency offset from the output signal 212, or at a fixed frequency.

Next, at step 415, the first and reference signal 212, 222 are mixed together to generate a first down-converted signal 242 based on the output and reference signals 212, 222. Then at step 417, the first down-converted signal 242 is sampled and processed to determine the frequency of the output signal 212.

Next, at step 420, it is determined whether the frequency of the output signal 212 is within a predefined range. The predefined range may be a range set by user or controller 22, or optionally, the predefined range may be set to a required ISM band. If the controller 22 determines that frequency difference between the output signal 212 and the reference signal is not within the predefined range, then the controller 22 and/or user may adjust the frequency of the output signal 212 and/or adjust one or more other parameters of the generator 20 at step 425. Then the process 400 loops back to step 410 to recheck the adjusted output signal 212. Alternatively, the determination may be based on being greater than a threshold.

If the controller 22 determines the frequency of the output signal 212 is within a predefined range, then the process 400 continues to step 430, where the output signal 212 is amplified. Then at step 435, the output signal 212 and reference signal 222 are mixed together to generate a second down-converted signal 272. Next at step 437, the second down-converted signal 272 is sampled to determine a phase of the second down-converted signal 272. The phase of the second down-converted signal 272 represents the phase shift of the output signal 212.

Next at step 440, the controller 222 determines whether the phase of the output signal is within the predefined range. Alternatively, the phase may be compared to a predetermined threshold. The predetermined threshold may be any range specified by the user or the controller 22. If the phase is not within the predefined range, then the process 400 goes to step 425, where the frequency is adjusted or alternatively the gain of the amplifier is adjusted. Then the process 400 returns to step 410 to recheck the frequency and phase shift of the output signal 212. If the phase shift is within the predefined range, then the process 400 ends at step 445.

Figure 5:
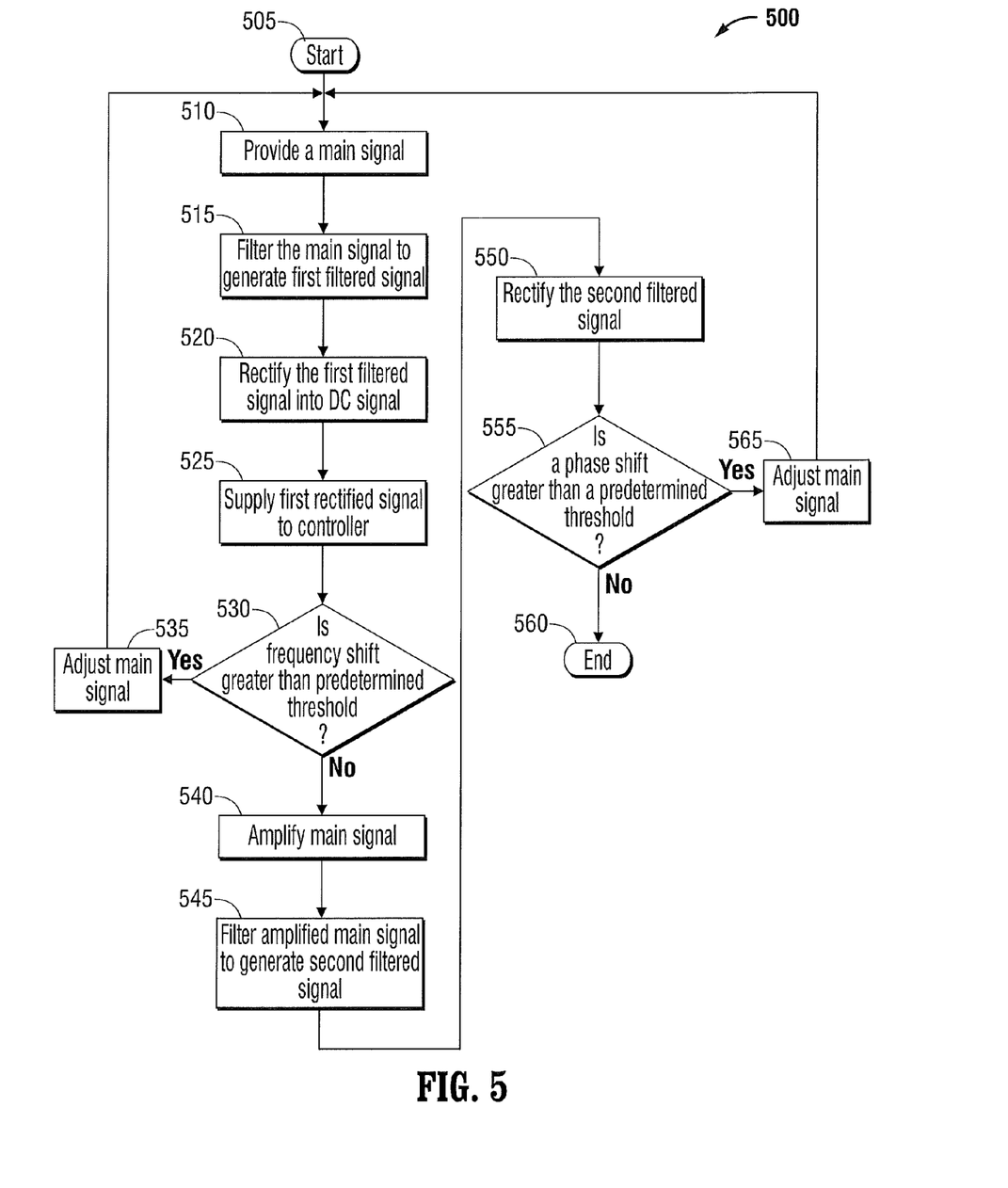
FIG. 5 is a flow diagram of a method for maintaining an output frequency of a medical device using the analog approach of FIG. 3 in accordance with another illustrative embodiment of the present disclosure.

FIG. 5 illustrates a flow diagram for maintaining an output frequency of a generator 20. The process 500 starts at step 505 and at step 510, in which a main signal, e.g., the output signal 212, is generated by a first oscillator 210. The first oscillator 210 is controlled by controller 22. Next at step 515, the main signal 212 is filtered using a first filter 320. The first filter 320 attenuates the main signal 212 as the frequency of the main signal 212 moves away from the center frequency of the first filter 320. The first filtered signal 332 is then sent to a rectifier 330. The rectifier 330 rectifies the first filtered signal 332 and provides a first rectified signal 532 to the controller at step 520.

Next, the controller 22 and/or microprocessor 122 sample the first rectified signal 532 to determine a frequency shift. Then, at step 530, the controller 22 determines that the frequency shift is greater than a predetermined threshold or outside a predefined range, then at step 535, the main signal 212 is adjusted. The main signal 212 may be adjusted by the user and/or controller and may include adjusting the frequency and/or other parameters of the generator 20.

If the controller 22 determines that the frequency shift is less than or equal to a predetermined threshold or within a predefined range, then at step 540, the main signal 212 is amplified. The amplified main signal 262 is supplied to a second filter 340. Then, at step 545, the second filter 340 generates a second filtered signal 342 by attenuating the amplified main signal 262 as the amplified main signal 262 moves away from the center frequency of the second filter 340. Optimally, the center frequency of the second filter 340 is set to zero to show any phase shift greater to or less than zero. The second filtered signal 342 is provided to rectifier 350. At step 530, the rectifier 350 rectifies the second filtered signal 342 and outputs a second rectified signal 352 to the controller 22. The controller 22 and/or microprocessor 122 then sample the second rectified signal 352 to determine a phase shift. Then at step 555, the controller 22 determines if the phase shift is greater than a predetermined threshold or outside a predefined range. If yes, then the main signal 212 is adjusted and/or the gain compensation of amplifier 250 is adjusted. If not, then the process 500 ends at step 565.

As various changes could be made in the above constructions without departing from the scope of the disclosure, it is intended that all matter contained in the above description shall be interpreted as illustrative and not in a limiting sense. It will be seen that several objects of the disclosure are achieved and other advantageous results attained, as defined by the scope of the following claims.

What is claimed is:

1. A system for measuring a characteristic of an output signal generated by a generator, the output signal having a first frequency, the system comprising:
    an oscillator configured to provide a reference signal having a second frequency;
    a first mixer configured to generate a first down-converted signal based on the output signal and the reference signal;
    an amplifier configured to amplify the output signal;
    a second mixer configured to generate a second, down-converted signal based on the amplified output signal and the reference signal; and
    a controller configured to:
        operate at a clock frequency lower than the first frequency;
        determine a frequency of the output signal based on the first down-converted signal; and
        determine a phase of the amplified output signal based on the second, down-converted signal.

2. The system according to claim 1, wherein the output signal is a digital signal or an analog signal.

3. The system according to claim 1, wherein the controller is further configured to control the output signal based on the determined frequency of the output signal.

4. The system according to claim 1, wherein the reference signal is a signal having a fixed or variable frequency.

5. The system according to claim 1, wherein the second frequency is set to a frequency such that the difference between the first and second frequencies is less than the clock frequency of the generator.

6. The system according to claim 1, wherein the second frequency is set equal to the first frequency.

7. The system according to claim 1, wherein the second frequency is set to a frequency offset from the first frequency.

8. The system according to claim 1, wherein the output signal is a DC value when the output signal and the reference signal are locked to the same frequency.

9. The system according to claim 1, further comprising one or more sensors coupled to an output of the amplifier, the one or more sensors configured to sense the amplified output signal and provide the sensed, amplified output signal to the second mixer.

10. A system for measuring a high frequency output signal generated by a generator, the system comprising:
    a first filter having a first center frequency, the first filter configured to filter the output signal to obtain a first filtered signal;
    a first rectifier configured to rectify the first filtered signal to obtain a first rectified signal;
    an amplifier configured to amplify the output signal;
    a second filter having a second center frequency, the second filter configured to filter the amplified signal to obtain a second filtered signal;
    a second rectifier configured to rectify the second filtered signal to obtain a second rectified signal; and
    a microprocessor configured to:
        sample the first rectified signal;
        determine a frequency of the output signal based on the level of the first rectified signal;
        sample the second rectified signal; and
        determine a phase of the amplified output signal based on a level of the second rectified signal.

11. The system according to claim 10, wherein the first filter is a notch filter or a band-pass filter.

12. The system according to claim 10, wherein the first filter is configured to attenuate the output signal as the frequency of the output signal moves away from the first center frequency.

13. A method for measuring a characteristic of a high frequency output signal generated by a generator, the output signal having a first frequency that is higher than a clock frequency of a processor of the generator, the method comprising:
    generating a reference signal having a second frequency;
    mixing the output signal and the reference signal to generate a first down-converted signal;
    determining the characteristic of the output signal based on the first down-converted signal;
    amplifying the output signal;
    mixing the amplified output signal and the reference signal to obtain a second down-converted signal; and
    determining a phase of the amplified output signal based on the second down-converted signal.

14. The method according to claim 13, wherein the characteristic is frequency or phase reference signal.

15. The method according to claim 14, further comprising verifying whether the characteristic of the output signal is within a predetermined range.

16. The method according to claim 14, further comprising adjusting the first frequency of the output signal to achieve a desired output impedance of the generator.

* * * * *